United States Patent
Schectman

Patent Number: 5,865,770
Date of Patent: Feb. 2, 1999

[54] DEVICE TO COUNTERACT PARALYSIS

[76] Inventor: Leonard A. Schectman, 5568 Balfrey Dr., West Palm Beach, Fla. 33413

[21] Appl. No.: 760,483

[22] Filed: Dec. 5, 1996

Related U.S. Application Data

[60] Provisional application No. 60/008,243 Dec. 6, 1995.

[51] Int. Cl.$^6$ ........................................ A61H 1/00
[52] U.S. Cl. .................... 601/23; 601/33; 601/40; 623/24
[58] Field of Search ............... 601/5, 23, 33–35, 601/40; 623/24

[56] References Cited

U.S. PATENT DOCUMENTS

| | | | |
|---|---|---|---|
| 3,323,518 | 6/1967 | Swanson | 601/33 |
| 4,716,889 | 1/1988 | Saringer | 601/40 |
| 4,842,607 | 6/1989 | Repperger et al. | 623/24 |
| 5,080,682 | 1/1992 | Schectman | 623/24 |
| 5,117,814 | 6/1992 | Luttrell et al. | 601/23 |
| 5,178,137 | 1/1993 | Gour et al. | 601/40 |
| 5,252,102 | 10/1993 | Singer et al. | 623/24 |
| 5,303,696 | 4/1994 | Boice | 601/40 |
| 5,326,369 | 7/1994 | Schectman | 623/24 |

*Primary Examiner*—Jeanne M. Clark
*Attorney, Agent, or Firm*—Malin, Haley, DiMaggio & Crosby,PA

[57] ABSTRACT

A flexible lead screw and motor combination is provided that attaches to the body and has the ability to move body parts. The invention contains at least one motor actuated cincture screw that transfers torque over an articulating joint of the body. A high torque motor is mounted on a suitable location of the body, on one side of the articulating joint to be moved. The motor is attached, through a cable having an externally threaded cincture, to an internally threaded guide bushing mounted to a body location on the opposite side of the articulating joint. In certain mounting locations, the cable routing will be redirected by guide rings before entering the guide bushing. Activation of the motor rotates the cable and, depending on the threads and the direction of rotation chosen, either pulls the threaded guide bushing toward, or away from the motor. Thus, the joint lying between the attached motor and attached guide bushing can be either closed or opened.

2 Claims, 4 Drawing Sheets

DEVICE TO COUNTERACT PARALYSIS

This application claims the benefit of U.S. Provisional Application No. 60/008,243, filed Dec. 6, 1995.

BACKGROUND OF THE INVENTION

1. Field of the Invention

This invention relates generally to motion transfer and, more specifically, to a device for robotically moving parts of the body by the high speed transfer of torque through flexible screw-like cinctures.

2. Background information

U.S. Pat. No. 5,326,369, (369) issued to the instant inventor, teaches the use of a flexible lead screw device that provides motion transfer around corners without loss of propagated torque. The disclosure of 369, incorporated herein by reference, required hinged attachment of at least one articulating member to a support platform. A high torque motor, also mounted on the platform, was connected to the articulating member via a cable. The cable had at least one externally threaded cincture which engaged a threaded guide bushing attached to the articulating member. The articulating member thereby rotated about its hinged attachment in accordance with rotation, by the motor, of the cable and threaded cincture. By utilizing multiple members hingedly attached to the articulating member, and having a predetermined threaded engagement of the cable, cincture, and guide bushing connections, the device could move all the members according to the rotational output of the motor.

The disclosure of 369 used an artificial hand prosthesis as an example of the application of multiple articulating members. There exists a need for a device that performs analogously to the artificial hand prosthesis, but acts directly on the body.

While the connection of a guide bushing to each articulating member, and the use of multiple threaded cinctures, works well on an artificial prosthesis, the problems encountered in applying this device to a hand, or other body part, become apparent.

SUMMARY OF THE INVENTION

The present invention satisfies this need by providing a flexible lead screw device that attaches to the body and has the ability to move body parts. In general, the instant invention contains at least one motor actuated screw that transfers torque over an articulating joint of the body.

A high torque motor is mounted on a suitable location of the body, on one side of the articulating joint to be moved. The motor is attached, through a cable having an externally threaded cincture, to an internally threaded guide bushing mounted to a body location on the opposite side of the articulating joint. In certain mounting locations, the cable routing will be redirected by guide rings before entering the guide bushing.

Activation of the motor rotates the cable and, depending on the threads and the direction of rotation chosen, either pulls the threaded guide bushing toward, or away from the motor. Thus, the joint lying between the attached motor and attached guide bushing can be either closed or opened.

The actuation of a single joint can be accomplished using more than one motor-screw-bushing assembly to achieve complex and precise motion of the joint. Multiple joints can be similarly actuated providing complex and precise motion of a plurality of body parts.

The motor-screw-bushing assembly can be attached to the body using any type of suitable fasteners, such as hook and loop (VELCRO) fasteners. Alternatively, the assembly can be mounted on clothing-like devices that are worn around the desired areas of mobility. The clothing-like devices vary in complexity from a single glove to an entire body suit.

The motors can be controlled in various fashions depending on the needs of individual subjects. Control could be by voice activation, computer generation, programmable controller, or by other means not yet developed, such as nerve impulse.

Accordingly, a primary objective of the present invention is to provide a means for artificial movement of weak or paralyzed body parts by the transmission of torque about articulating joints.

Another objective of the present invention is to permit precise and complex motion of joints by predetermined attachment of multiple torque transfer devices on the body.

Still another objective of the present invention is to provide clothing-like devices that can be worn to provide mobility of paralyzed, or weak, body parts.

A further objective of the present invention is to provide a device that can be worn and used to exercise portions of the body that have recently undergone surgery. An example of which is a glove-like device worn by a patient that has undergone hand, or wrist, surgery and must exercise the hand to regain full motion.

In accordance with these and other objects which will become apparent hereinafter, the instant invention will now be described with particular reference to the accompanying drawings.

DESCRIPTION OF THE PREFERRED EMBODIMENTS

Figure 1:
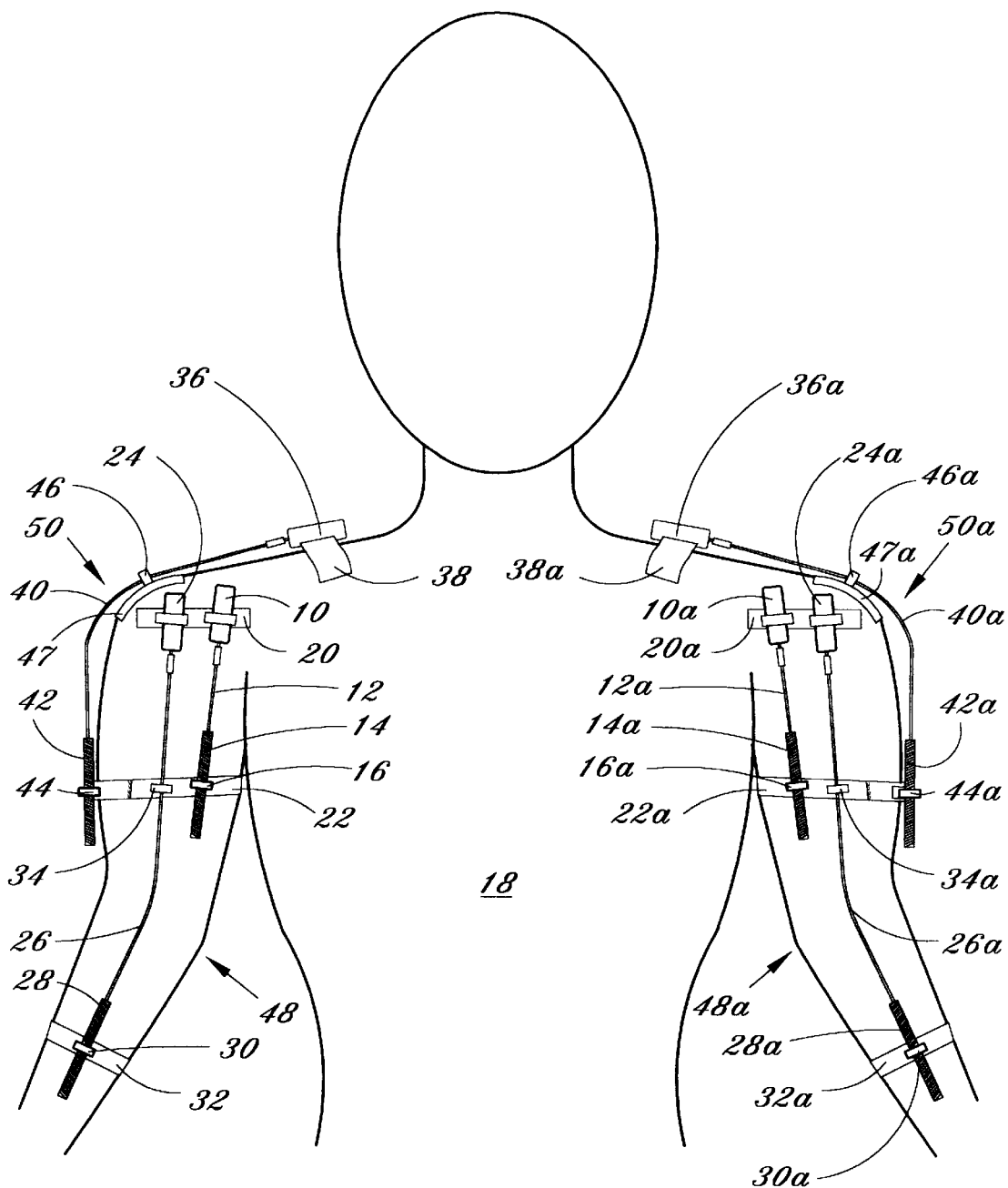
FIG. 1 is a plan view of the present invention in an embodiment for both elbow and shoulder motion.

The present invention is described in four specific embodiments. It will be apparent to those skilled in the art that various modifications, substitutions, and rearrangements can be made without departing from the spirit of the invention. Therefore, the invention is not to be considered limited to what is described in the specification and shown in the drawings.

Referring now to the drawings and specifically to FIG. 1, the present invention can be seen in an embodiment configured for shoulder and elbow movement. High torque motor (motor) 10 is connected by cable 12 to externally threaded cincture screw 14. Externally threaded cincture screw 14 (hereinafter referred to as "cincture") threads into internally threaded guide bushing 16 (hereinafter referred to as "guide bushing"). This assembly, incorporated into Applicant's present invention, is fully described in Applicant's flexible screw invention, U.S. Pat. No. 5,326,369, the disclosure of which is incorporated herein by reference.

Figure 2:
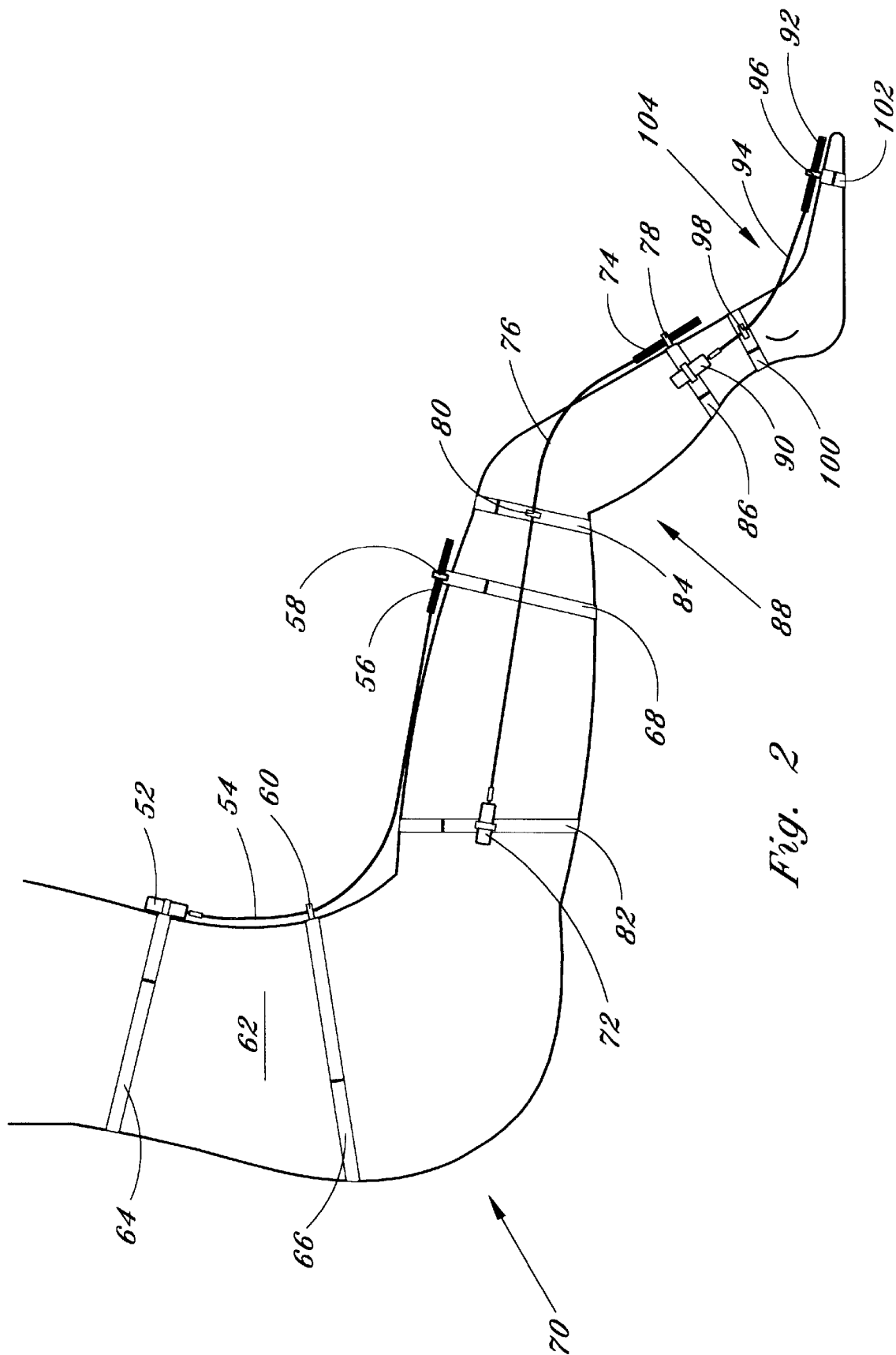
FIG. 2 is a plan view of the present invention in an embodiment for hip, knee, and foot motion.
Figure 3:
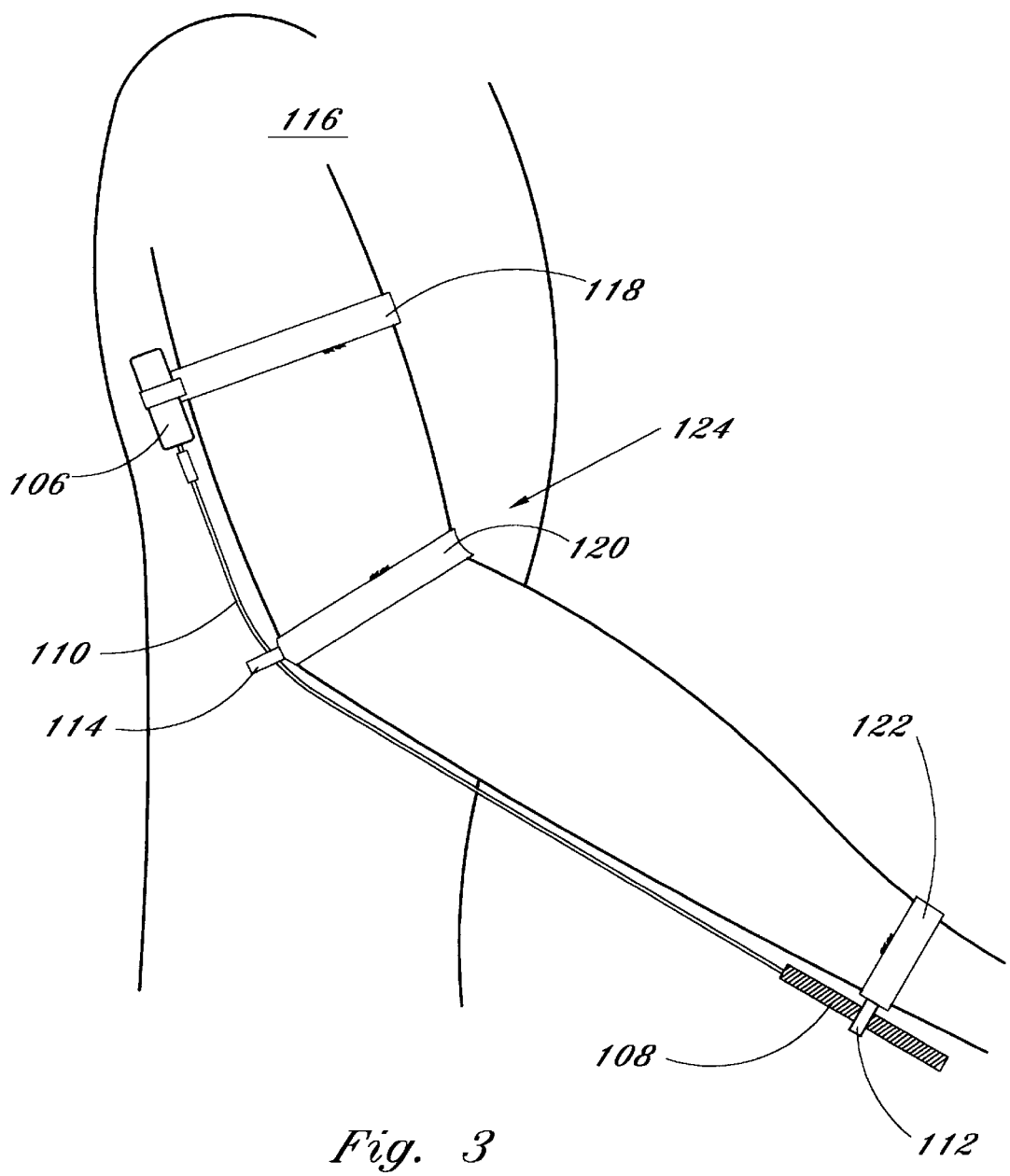
FIG. 3 is a plan view of the present invention in an embodiment for elbow motion.

High torque motor 10 is connected to body 18 by fastener 20. (Fastener 20, and all other fasteners used to connect the invention to the body identified in FIGS. 1–3, are suitable fasteners, such as hook and loop (VELCRO®) type fasteners). Fastener 20 may be longer and wrap around the arm in suitable fashion (not shown). Threaded guide bushing 16 is connected to body 18 by fastener 22.

Motor 24, connected to body 18 by fastener 20, is connected by cable 26 to cincture 28. Cincture 28 threads into threaded guide bushing 30. Threaded guide bushing 30 is attached to body 18 by fastener 32. Cable 26 is guided from motor 24 to guide bushing 30 by guide ring 34. Guide ring 34 is attached to body 18 by fastener 22.

Motor 36, attached to body 18 by fastener 38, is connected to cincture 42 by cable 40. Fastener 38 may be longer and wrap around the shoulder in suitable fashion (not shown). Cincture 42 threads into threaded guide bushing 44 which is attached to body 18 by fastener 22. Cable 40 is guided between motor 36 and guide bushing 44 by guide ring 46. Guide ring 46 is attached to body 18 by fastener 47. Fastener 47 may be longer and wrap around the shoulder in suitable fashion (not shown).

In operation, motor 24, cable 26, cincture 28, guide bushing 30, guide ring 34, and fasteners 20, 22, and 32 provide movement of elbow joint 48 of body 18. Likewise, motors 10 and 36, cables 12 and 40, cinctures 14 and 42, guide bushings 22 and 44, guide ring 46, and fasteners 20, 22, and 38 provide movement of shoulder 50 of body 18.

The side of body 18 opposite shoulder 50 and elbow 48 contains a mirror image of identical components identified by reference numerals ending with the letter "a". The description of the components on the opposite side of body 18 is identical to the above description with the reference numerals appended with the letter "a". Therefore, to avoid redundancy, the description of components on the side of body 18 containing shoulder 50a and elbow 48a will not be repeated here.

Now referring to FIG. 2, motor 52 is connected to cincture 56 by cable 54. Cincture 56 is threaded into guide bushing 58. Cable 54 is guided from motor 52 to guide bushing 58 by guide ring 60. Motor 52 is attached to body 62 by fastener 64. Guide ring 60 is attached to body 62 by fastener 66. Guide bushing 58 is attached to body 62 by fastener 68. In operation, motor 52, guide ring 60, cable 54, cincture 56, guide bushing 58 and fasteners 64, 66, and 68 provide motion of hip joint 70.

Motor 72 is connected to cincture 74 by cable 76. Cincture 76 is threaded into guide bushing 78. Cable 76 is guided from motor 72 to guide bushing 78 by guide ring 80. Motor 72 is attached to body 62 by fastener 82. Guide ring 80 is attached to body 62 by fastener 84. Guide bushing 78 is attached to body 62 by fastener 86. In operation, motor 72, cable 76, cincture 74, guide bushing 78, guide ring 80, and fasteners 82, 84, and 86 provide movement of knee joint 88.

Motor 90 is connected to cincture 92 by cable 94. Cincture 92 is threaded into guide bushing 96. Cable 94 is guided from motor 90 to guide bushing 96 by guide ring 98. Motor 90 is attached to body 62 by fastener 86. Guide ring 98 is attached to body 62 by fastener 100. Guide bushing 96 is attached to body 62 by fastener 102. In operation, motor 90, cable 94, cincture 92, guide bushing 96, guide ring 98, and fasteners 86, 100, and 102 provide movement of ankle 104.

In combination the above described components provide movement for the hip 70, knee 88, and ankle 104 of body 62. If needed, the other leg of body 62 could be outfitted with a mirror image of these components (not shown) to provide movement of both legs.

Now referring to FIG. 3, motor 106 is connected to cincture 108 by cable 110. Cincture 108 is threaded into guide bushing 112. Cable 110 is guided from motor 106 to guide bushing 112 by guide ring 114. Motor 106 is attached to body 116 by fastener 118. Guide ring 114 is attached to body 116 by fastener 120. Guide bushing 112 is attached to body 116 by fastener 122. In operation, motor 106, cable 110, cincture 108, guide bushing 112, guide ring 114 and fasteners 118, 120, and 122 provide movement of elbow 124.

Figure 4:
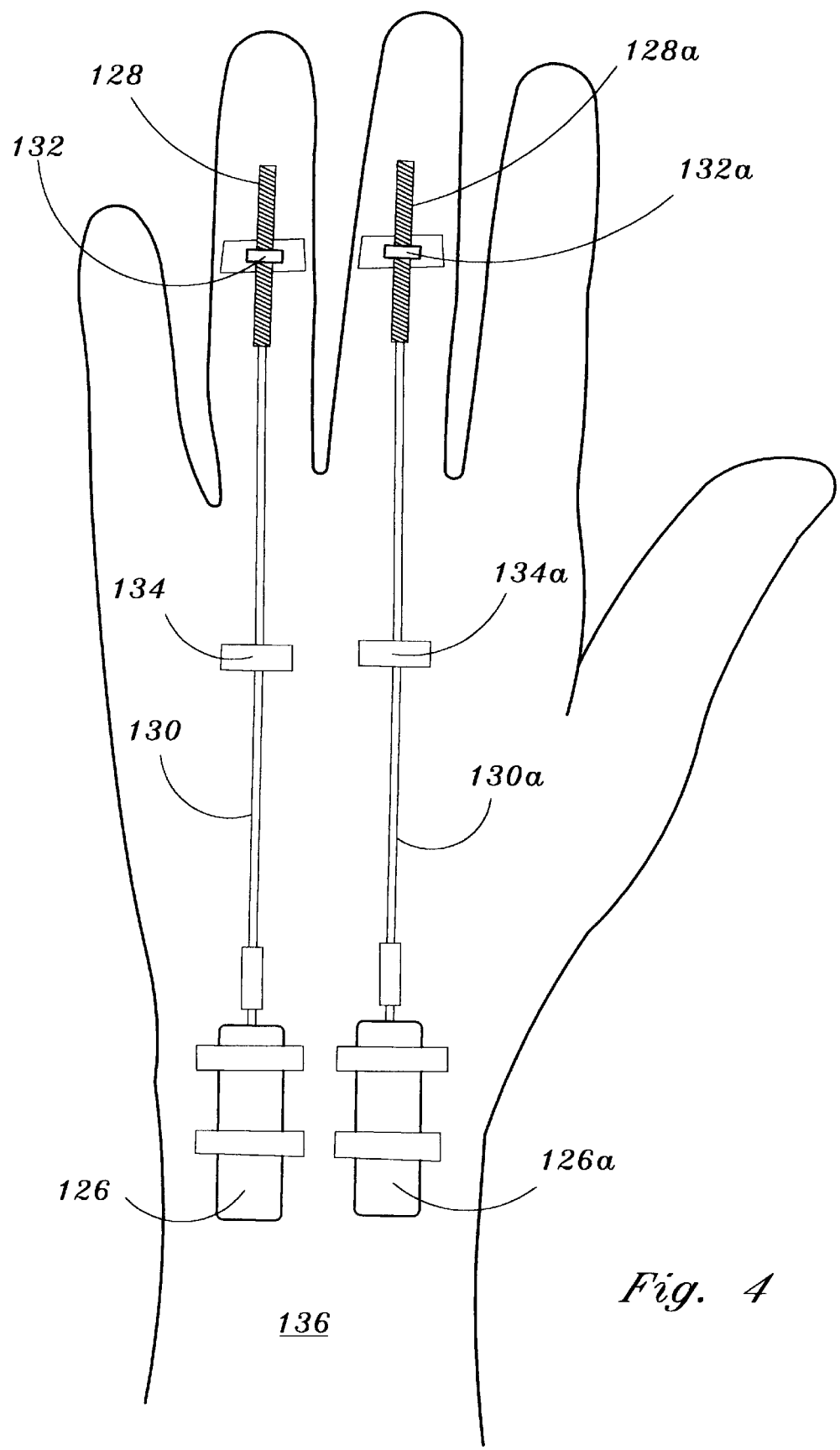
FIG. 4 is a plan view of the present invention in a glove embodiment for hand motion.

Now referring to FIG. 4, an embodiment is shown wherein the components are attached to a fitted glove which is worn on the hand of a subject. Motor 126 is connected to cincture 128 by cable 130. Cincture 128 is threaded into guide bushing 132. Cable 130 is guided from motor 126 to guide bushing 132 by guide ring 134. Motor 126, guide ring 134, and guide bushing 132 are attached to glove 136, in the locations shown in FIG. 4, by a suitable method such as epoxy cement.

In a similar manner, motor 126a is connected to cincture 128a by cable 130a. Cincture 128a is threaded into guide bushing 132a. Cable 130a is guided from motor 126a to guide bushing 132a by guide ring 134a. Motor 126a, guide ring 134a, and guide bushing 132a are attached to glove 136, in the locations shown in FIG. 4, by a suitable method such as epoxy cement.

Glove 136 is fitted to the subject and worn to provide movement of a weak or paralyzed hand. The invention will provide exercise for the relief of stiffness or any other application that requires forced hand movement. The embodiment of a separate garment that is worn by the subject can be extended to other desired motions.

If the motion desired was to the subject's shoulders and elbows, then the article of clothing, in this case a jacket-like garment (not shown), would contain an arrangement of the present invention similar to that disclosed in FIG. 1, except the attachment of the components would be to the clothing-like apparatus instead of directly onto the body.

If the motion desired was the subject's hip, knee, and foot, then the arrangement of the present invention, in the pants or trouser-like garment (not shown), would be similar to that disclosed in FIG. 2.

Likewise, if the motion desired was to the subject's elbow, then the garment (not shown) would be similar in configuration to the invention as disclosed in FIG. 3.

The motors shown in FIGS. 1–4 are controlled by a motor controller (not shown) receiving control input in various manners depending on the needs of the subject. Motor control can be by voice activation, computer generation, programmable controller, simple switching, or other suitable methods.

The various embodiments of the present invention shown in FIGS. 1–4, can be combined, either directly on the body or in garments worn on the body, or both, to facilitate movement of various combinations of body parts. An entire body suit could be worn to provide movement to weak or totally paralyzed subjects.

The instant invention has been shown and described herein in what is considered to be the most practical and preferred embodiments. It is recognized, however, that departures may be made therefrom within the scope of the invention and that obvious modifications will occur to a person skilled in the art.

What is claimed is:

1. An apparatus to counteract paralysis by movement of a plurality of articulated joints of a person by using torque transfer, comprising:

a plurality of high torque motors, each motor including means for mounting on a first side of each articular joint at spaced apart locations from the other motors;

a plurality of cables, each cable coupled to a respective one of the high torque motors, each cable having at least one externally threaded cincture coupled to said cable;

a plurality of internally threaded guide bushings, each guide bushing operatively associated with a respective one of the externally threaded cinctures, each internally threaded guide bushing including means for mounting on a second side of each articulated joint at spaced apart locations from the other internally threaded guide bushings;

said motors causing the rotation, in a preselected direction, of said cables and said externally threaded cinctures through said internally threaded guide bushings, causing the first and the second sides of each articulated joint to move in direct response to said motor rotation to articulate the joints, wherein each of the plurality of articulated joints are simultaneously moveable in different planes of direction to counteract paralysis of a given body part of the person.

2. The apparatus according to claim 1, including means for guiding said cables connected between said high torque motors and said internally threaded guide bushings.

* * * * *